(12) United States Patent
Marumori et al.

(10) Patent No.: US 8,784,100 B2
(45) Date of Patent: Jul. 22, 2014

(54) IMPRESSION TRAY FOR LOWER JAW

(71) Applicant: GC Corporation, Bunkyo-ku (JP)

(72) Inventors: Hidefumi Marumori, Yokohama (JP); Hiroshi Kamohara, Matsudo (JP)

(73) Assignee: GC Corporation, Bunkyo-ku (JP)

( * ) Notice: Subject to any disclaimer, the term of this patent is extended or adjusted under 35 U.S.C. 154(b) by 0 days.

(21) Appl. No.: 13/782,397

(22) Filed: Mar. 1, 2013

(65) Prior Publication Data
US 2013/0230824 A1  Sep. 5, 2013

(30) Foreign Application Priority Data

Mar. 2, 2012 (JP) ................................ 2012-046410

(51) Int. Cl.
*A61C 9/00* (2006.01)
(52) U.S. Cl.
CPC .................................. *A61C 9/0006* (2013.01)
USPC ........................................................... 433/37
(58) Field of Classification Search
USPC ......................................... 433/37, 41, 45, 46
See application file for complete search history.

(56) References Cited

U.S. PATENT DOCUMENTS

| 3,473,225 | A | * | 10/1969 | Deuschle et al. | ................ 433/48 |
| 5,076,785 | A | * | 12/1991 | Tsai | .................................. 433/46 |
| 5,336,086 | A | * | 8/1994 | Simmen et al. | .................. 433/37 |
| 5,752,826 | A | | 5/1998 | Andreiko | |
| 6,079,977 | A | * | 6/2000 | Persichetti | ........................ 433/37 |
| 7,273,371 | B2 | * | 9/2007 | Massad | ............................ 433/37 |
| D571,473 | S | * | 6/2008 | Wilkens | ........................ D24/181 |
| D632,395 | S | * | 2/2011 | Massad | .......................... D24/181 |
| D686,733 | S | * | 7/2013 | Marumori et al. | ............. D24/181 |
| 2005/0106529 | A1 | | 5/2005 | Abolfathi et al. | |

FOREIGN PATENT DOCUMENTS

JP  2000-135227 A  5/2000
JP  2013-75092 A  4/2013

OTHER PUBLICATIONS

U.S. Appl. No. 13/853,482, filed Mar. 29, 2013, Marumori, et al.
U.S. Appl. No. 13/853,420, filed Mar. 29, 2013, Marumori, et al.

* cited by examiner

*Primary Examiner* — Ralph Lewis
(74) *Attorney, Agent, or Firm* — Oblon, Spivak, McClelland, Maier & Neustadt, L.L.P.

(57) ABSTRACT

The invention provides a plastic impression tray for a lower jaw having an outer wall, an inner wall and a bottom portion and forming a U-shaped flat surface. A rim with a particular height is provided along each of upper ends of the outer wall and the inner wall, through holes with particular widths are provided with a particular relationship between the distance between the adjacent through holes and a width of the through hole, circular through holes with particular diameters are provided between the through holes in the bottom portion, and bottom portion through holes with particular widths and lengths are provided on a line connecting the bottom portion sides of the through holes which are positioned at the closest side to the end portion of the U-shaped portion in the end portion thereof, or in a closer side to the end portion than the line, respectively.

8 Claims, 3 Drawing Sheets

IMPRESSION TRAY FOR LOWER JAW

BACKGROUND OF THE INVENTION

1. Field of the Invention

The present invention relates to a plastic impression tray for a lower jaw to be used at a time of taking an impression within an oral cavity of a lower jaw as a preparation stage for preparing a complete denture as a prosthesis in dentistry, wherein the impression tray can prevent a set impression material from floating upward from the tray and being peeled off from the tray, and can be used for taking an impression with high accuracy.

2. Description of the Conventional Art

In a dental care, an impression material such as a silicone impression material or an alginate impression material has been used at a time of taking an impression within an oral cavity as a preparation stage for preparing a prosthesis. For inserting and holding such an impression material within the oral cavity, an impression tray has been used. In the impression taking, the impression material is loaded onto the impression tray so as to be inserted into the oral cavity of a patient, the impression material is pressed into the oral cavity of the patient to be carried out the impression taking, the impression material is set, and the impression material is thereafter taken out from the oral cavity of the patient integrally in a state in which the set impression material is retained in the impression tray.

A large force is necessary at a time of taking out the set impression material from the oral cavity. As a result, there is a problem that the set impression material floats upward from the impression tray and is peeled off from the impression tray, so that an air gap is generated between the impression tray and the impression material. In the case that the air gap is generated, it is often the case that the impression material deforms from the initial set state, and an accuracy of the prepared dental prosthesis is significantly lowered. Further, since the impression material has a property that the impression material is shrinked by a reaction and a volatilization of a water content after being set, the impression material is greatly affected by the shrinkage in the case that the impression material is peeled off from the impression tray, whereby an accuracy of the dental prosthesis is further lowered. Accordingly, for the impression tray, there becomes important a performance that the impression material inserted into the oral cavity of the patient so as to be set can be taken out from the oral cavity of the patient without being deformed.

Generally, the impression tray is provided with a retention hole or groove for mechanically retaining the set impression material. In other words, the impression material paste before being set enters into the retention hole and is set, whereby the set impression material and the tray are mechanically engaged. Particularly, since the set impression material tends to be peeled off in a tray peripheral portion, an application of an undercut (a rib) is carried out along the peripheral portion. However, since a sufficient amount of impression material cannot enter into the undercut portion, the peeling tends to be generated in the peripheral portion. Further, the impression tray is made of a metal or a plastic, and the metal tray can be easily provided with an undercut having a height from 1.5 to 2.5 mm in the peripheral portion by processing as mentioned above. On the other hand, since the plastic tray is affected by a metal mold which is used at a time of producing the tray and the molded tray cannot be taken out, the plastic tray cannot be provided with an undercut portion having an effective height. Therefore, particularly in the impression tray made of a plastic, there has been a problem that the peeling of the impression material from the tray peripheral portion is large, and a deformation becomes larger.

As the tray made of a plastic, there is a dental impression tray which is provided with a bottom wall, and inner and outer walls for forming an impression material retaining concave portion which is similar to a tooth row shape and is formed as a curved shape in a plan view, is provided with a handle portion which extends forward from side ends of front teeth in the bottom wall or the outer wall, and is provided at least in the inner and outer walls of the concave portion with a lot of impression material retention holes which inhibit a relative movement to the impression material over a whole surface (refer, for example, to patent document 1). The patent document 1 exemplifies a structure in which impression material retention holes provided in inner and outer opposed walls are elongated holes which are elongated in a vertical direction and penetrate in an inward and outward direction of the concave portion (refer to claim 2), and the impression material retention hole provided in a front teeth side of the outer wall is provided in the bottom wall of the concave portion or the handle portion, or both of them and is communicated in a penetrating manner (refer to claim 3). However, the patent document 1 shows only the structure in which a distance between the adjacent elongated holes in the drawing is very narrow in the impression material retention holes which are provided in the inner and outer opposed walls and elongated in the vertical direction as mentioned above, and any disclosure of a width of the elongated hole does not exist in the patent document 1. Further, the impression material retention hole provided in the front teeth side of the outer wall is disclosed as the elongated hole in the drawing, however, any disclosure of the distance between the adjacent elongated holes and the width of the elongated hole does not exist. Further, the impression material retention hole having a circular cross sectional shape is provided in the bottom wall, however, a hole diameter and a distance between the adjacent impression material retention holes having the circular cross section shape are not disclosed at all in the impression material retention hole having the circular cross sectional shape. Further, the bottom wall is shown as an aspect that a U-shaped end portion side (a back tooth side) becomes rapidly shallow.

In the dental impression tray described in the patent document 1 mentioned above, it is not assured that the impression material can be sufficiently retained by the impression material retention holes constructed by the elongated holes which are provided in the inner and outer opposed walls and are elongated in the vertical direction, it is not assured that the impression material can be sufficiently retained by the impression material retention hole which is provided in the front teeth side of the outer wall, and it is not assured that the impression material can be sufficiently retained by the impression material retention hole which is provided in the bottom wall and has the circular cross sectional shape. Further, there is a defect that the impression material in the end portion side (the back tooth side) of the U-shaped form tends to be peeled off.

SUMMARY OF THE INVENTION

Problem to be Solved by the Invention

An object of the present invention is to provide a plastic impression tray for a lower jaw to be used at a time of taking an impression within an oral cavity of a lower jaw as a preparation stage for preparing a complete denture as a prosthesis in dentistry, wherein the impression tray can prevent a set impression material from floating upward from the tray and being peeled off from the tray, and can be used for taking an impression with high accuracy.

Means for Solving the Problem

The inventors of the present invention have devoted themselves to make a study for solving the problem mentioned above. As a result, the inventors have inquired into a fact that the problem mentioned above can be solved by forming a whole shape of the plastic impression tray for a lower jaw as a shape having an outer wall which is inclined to an outer side via a circular arc shaped portion from an outer side of a bottom portion forming a U-shaped flat surface with an approximately uniform width and is reduced its height in an end portion side of the U-shaped portion, and an inner wall which is inclined to an inner side via a circular arc shaped portion from an inner side of the bottom portion, setting a rim having a height from 0.01 to 1 mm in the bottom portion side along each of upper ends of the outer wall and the inner wall, forming through holes each of which reaches the bottom portion from a portion just below the rim vertically to the rim and is formed as an elongated hole having a width from 1.5 to 4.0 mm in such a manner that a distance between the adjacent through holes is from 2 to 5 times the width of the through hole, forming in the bottom portion circular through holes each having a diameter from 3 to 6 mm in the center of the adjacent distances of the through holes which are provided in the outer wall and the inner wall and are formed as the elongated holes, and setting bottom portion through holes each of which has a width from 1.0 to 3.0 mm and a length from 5 to 15 mm and is formed as an elongated hole, on a line which connects the bottom portion side end portions of the respective elongated through holes positioned in the closest side to the end portions of the U-shaped portion in the outer wall and the inner wall in the end portions of the U-shaped portion, or sides which are closer to the end portions than the line, and the inventors have completed the present invention.

In the structure mentioned above, the inventors have inquired into a fact that it is preferable that the width of the through holes which are provided in the outer wall and the inner wall and are formed as the elongated holes is from 2.0 to 3.0 mm, the length is from 2 to 3 times the width, the distance of the through holes which are provided in the outer wall and the inner wall and are formed as the elongated holes is from 3 to 18 mm, the height of the rim is from 1 to 0.3 mm, and a rim having a height from 0.01 to 1 mm is provided in an opposite side to the bottom portion along each of the upper ends of the outer wall and the inner wall.

In other words, according to the present invention, there is provided a plastic impression tray for a lower jaw, the impression tray having an outer wall which is inclined to an outer side via a circular arc shaped portion from an outer side of a bottom portion forming a U-shaped flat surface with an approximately uniform width and is reduced its height in an end portion side of the U-shaped portion, and an inner wall which is inclined to an inner side via a circular arc shaped portion from an inner side of the bottom portion, wherein a rim having a height from 0.01 to 1 mm is provided in the bottom portion side along each of upper ends of the outer wall and the inner wall, through holes each of which reaches the bottom portion from a portion just below the rim vertically to the rim and is formed as an elongated hole having a width from 1.5 to 4.0 mm are formed in such a manner that a distance between the adjacent through holes is from 2 to 5 times the width of the through hole, in the bottom portion circular through holes each having a diameter from 3 to 6 mm are formed in the center of the adjacent distances of the through holes which are provided in the outer wall and the inner wall and are formed as the elongated holes, and bottom portion through holes each of which has a width from 1.0 to 3.0 mm and a length from 5 to 15 mm and is formed as an elongated hole are provided on a line which connects the bottom portion side end portions of the respective elongated through holes positioned in the closest side to the end portions of the U-shaped portion in the outer wall and the inner wall in the end portions of the U-shaped portion, or sides which are closer to the end portions than the line. In the impression tray for a lower jaw, it is preferable that the width of the through holes which are formed as the elongated holes is from 2.0 to 3.0 mm, the length is from 2 to 3 times the width, the distance of the through holes which are formed as the elongated holes is from 3 to 18 mm, the height of the rim is from 1 to 0.3 mm, and a rim having a height from 0.01 to 1 mm is provided in an opposite side to the bottom portion along each of the upper ends of the outer wall and the inner wall.

Effect of the Invention

Since the impression tray for a lower jaw according to the present invention is provided with the rims having the height from 0.01 to 1 mm, preferably from 0.1 to 0.3 mm, in the bottom portion side along each of the upper ends of the U-shaped outer wall and inner wall, the portion below the rim comes to an undercut portion, so that the set impression material is hard to float upward and be peeled off from the tray. Further, since the height of the rim is from 0.01 to 1 mm and is low, the rim does not form an obstacle to unloading from a metal mold at a time of an injection molding. Further, since the width of the through holes each of which reaches the bottom portion from the portion just below the rim vertically to the rims in the outer wall and the inner wall and is formed as the elongated hole is from 1.5 to 4.0 mm, and the distance between the adjacent through holes is from 2 to 5 times the width of the through hole, the impression material appropriately enters into the through holes at a time of loading up the silicone impression material or the alginate impression material within the tray so as to press to the lower jaw within the oral cavity of the patient, thereby taking the impression, and retains the set impression material, the set impression material is hard to float upward and be peeled off from the tray. Further, since the circular through holes each having the diameter from 3 to 6 mm are formed in the bottom portion at the center of the adjacent distances of the through holes which are provided in the outer wall and the inner wall and are formed as the elongated holes, the impression material enters into the circular through holes so as to retain the set impression material at a time of loading up the silicone impression material or the alginate impression material within the tray so as to press to the lower jaw within the oral cavity of the patient, thereby taking the impression. However, since the circular through holes do not exist on the line connecting the through holes which are provided in the outer wall and the inner wall and are formed as the elongated holes, the impression material loaded in the same portion within the tray is not pushed out to an outer side of the tray from the through holes which are provided in the outer wall and the inner wall and are formed as the elongated holes and the circular through holes which are provided in the bottom portion, and any space is not generated in the set impression material. Further, since the bottom portion through holes which have the width from 1.0 to 3.0 mm and the length from 5 to 15 mm and are formed as the elongated holes are provided on the line connecting the bottom portion side end portions of the through holes which are positioned in the closest side to the end portion of the U-shaped portion in the outer wall and the inner wall, or the sides which are closer to the end portions than the line, the impression material loaded in the closest side to the back tooth within the tray enters into the through holes which are provided in the outer wall and the inner wall in the end portions of the U-shaped portion and are formed as the elongated holes, and the bottom portion through holes which are provided in the bottom portion and are formed as the elongated holes so as to be firmly retained even if the height of the end portion side of the U-shaped portion of the outer wall is reduced in conformity to a shape of the oral cavity. Therefore, there is not generated the defect that the impression material in the end portion side (the back teeth side) of the U-shaped portion tends to be peeled off.

Further, in the impression tray for a lower jaw mentioned above, in the case that the width of the through holes which are provided in the outer wall and the inner wall and are formed as the elongated holes is from 2.0 to 3.0 mm, the length thereof is from 2 to 3 times the width, and the distance of the through holes which are provided in the outer wall and the inner wall and are formed as the elongated holes is from 3 to 18 mm, the impression material is better retained by the through holes formed as the elongated holes at a time of impression taking, and the set impression material is hard to float upward and be peeled off from the tray. Further, in the case that the rim having the height from 0.01 to 1 mm is provided in the opposite side to the bottom portion along each of the upper ends of the outer wall and the inner wall, a thickness of each of the upper ends of the U-shaped outer wall and inner wall is increased and a strength thereof is improved. However, the increase of the thickness does not form an obstacle to unloading from the metal mold at a time of the injection molding.

DETAILED DESCRIPTION OF THE PREFERRED EMBODIMENT

Figure 1:
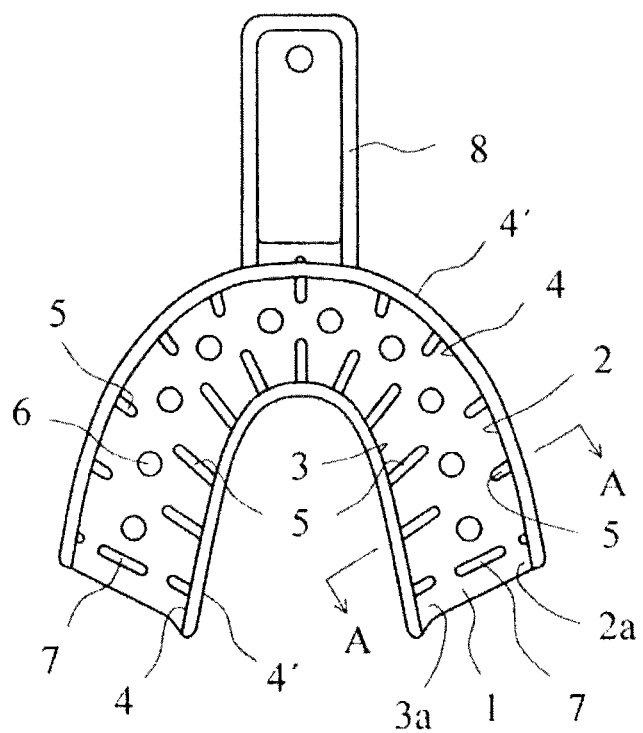
FIG. 1 is a plan view of an embodiment of an impression tray for a lower jaw according to the present invention.
Figure 2:
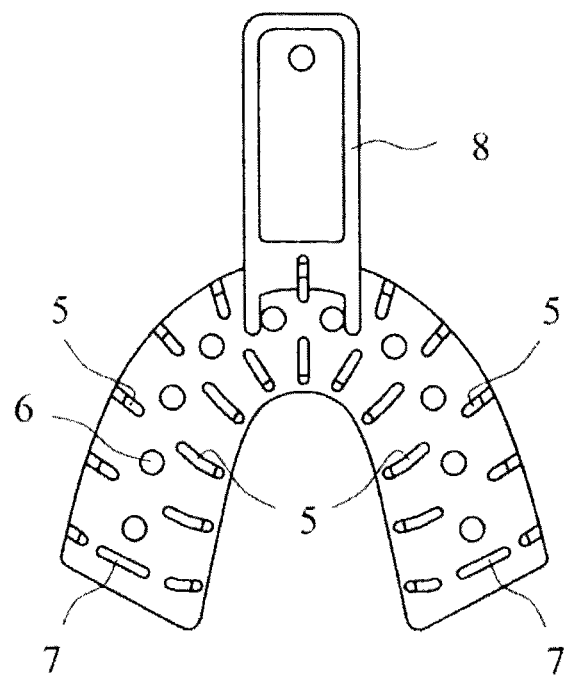
FIG. 2 is a back elevational view of the impression tray for a lower jaw shown in FIG. 1.
Figure 3:
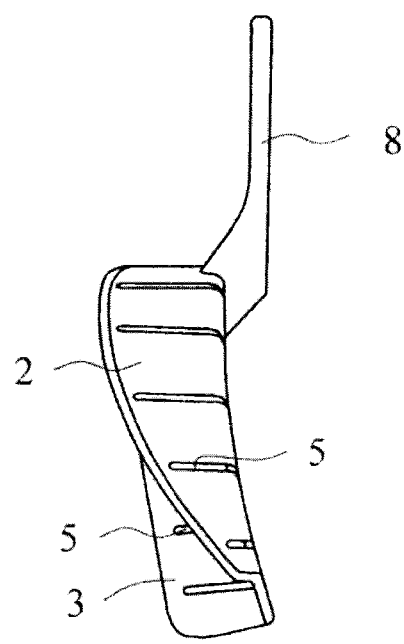
FIG. 3 is a right side elevational view of the impression tray for a lower jaw shown in FIG. 1.
Figure 4:
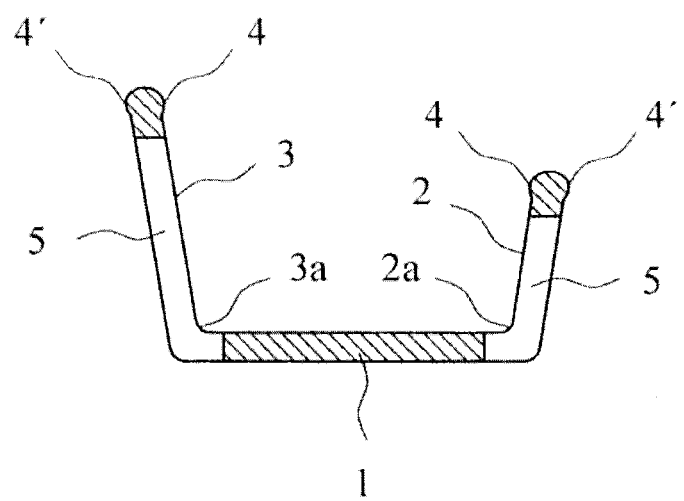
FIG. 4 is an enlarged end elevational view along a line A-A in FIG. 1.
Figure 5:
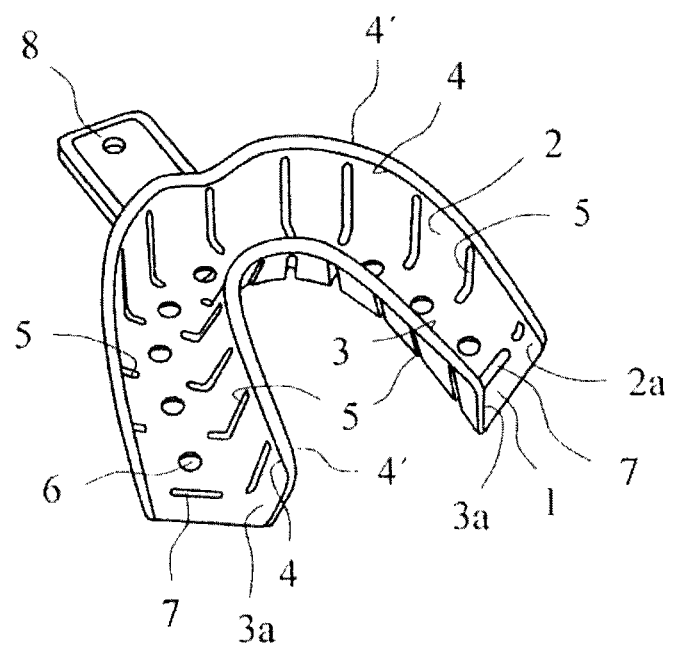
FIG. 5 is a perspective view of the impression tray for a lower jaw shown in FIG. 1.

An impression tray for a lower jaw according to the present invention is a plastic impression tray for a lower jaw, the impression tray having a bottom portion 1 which is formed as a U-shaped form and forms a flat surface with an approximately uniform width, an outer wall 2 which is inclined to an outer side via a circular arc shaped portion 2a from an outer side of the bottom portion 1 and is reduced its height in an end portion side of the U-shaped portion, and an inner wall 3 which is inclined to an inner side via a circular arc shaped portion 3a from an inner side of the bottom portion 1. Further, a rim 4 having a height from 0.01 to 1 mm, preferably from 0.1 to 0.3 mm is provided in a side of the bottom portion 1 along each of upper ends of the outer wall 2 and the inner wall 3. The rim 4 is provided for forming an undercut portion below the rim 4 so as to create an action of preventing a set impression material from floating upward and being peeled off from the tray. If the height of the rim 4 is less than 0.01 mm, an effect of forming the undercut portion cannot be expected, and if the height goes beyond 1 mm, the rim forms an obstacle to unloading from a metal mold at a time of injection molding of the tray due to its excessive height and it is impossible to well carry out the injection molding. Further, in the case a rim 4' having a height from 0.01 to 1 mm is further provided in an opposite side to the bottom portion 1 along each of the upper ends of the outer wall 2 and the inner wall 3, a thickness of each of the upper ends of the U-shaped outer wall 2 and inner wall 3 is increased and a strength thereof is improved. However, the rim 4' does not form an obstacle to unloading from the metal mold at a time of the injection molding and is preferably provided.

Reference numeral 5 denotes a through hole which is provided vertically to the rim 4 in the outer wall 2 and the inner wall 3, is from 1.5 to 4.0 mm in a width reaching the bottom portion 1 from a portion just below the rim 4, and is formed as an elongated hole. The through hole 5 is formed such that a distance between the adjacent through holes 5 is approximately equal to 2 to 5 times the width of the through hole 5. If the width of the elongated through hole 5 is less than 1.5 mm, the impression material does not appropriately enter into the through holes 5 at a time of loading a silicone impression material or an alginate impression material in the tray and pressing to a lower jaw within an oral cavity of a patient so as to take an impression, and a phenomenon that the set impression material cannot be retained and falls off is generated. Accordingly, this width is not preferable. If the width goes beyond 4.0 mm, a pressure is insufficient only by loading the silicone impression material or the alginate impression material in the tray and pressing to the lower jaw within the oral cavity of the patient. Accordingly, a phenomenon that the impression material which cannot enter into the through holes 5 and is set cannot be retained and falls off is generated. Accordingly, this width is not preferable. Further, if the distance between the through hole 5 and the adjacent through hole 5 is less than 2 times the width of the through hole 5, the adjacent through holes 5 come too close to each other. Therefore, the impression material cannot sufficiently enter into the through holes 5 at a time of loading the silicone impression material or the alginate impression material in the tray and pressing to the lower jaw within the oral cavity of the patient so as to take the impression. Further, if the distance goes beyond fivefold, the adjacent through holes 5 are too away from each other. Therefore, there is not created the effect that the impression material sufficiently enters into the through holes 5 so as to be retained at a time of loading the silicone impression material or the alginate impression material in the tray and pressing to the lower jaw within the oral cavity of the patient so as to take the impression. Accordingly, this distance is not preferable. It is particularly preferable that the width of the elongated through hole 5 is from 2.0 to 3.0 mm, the length of the through hole 5 is from 2 to 3 times the width, and the distance between the adjacent through holes 5 is from 3 to 18 mm.

Reference numeral 6 denotes a circular through hole which is formed in the bottom portion 1 positioned at the center of the adjacent distances of the through holes 5 provided in the outer wall 2 and the inner wall 3 and formed as the elongated holes and has a diameter from 3 to 6 mm. It is necessary for the circular through hole 6 to be formed in the bottom portion 1 which is positioned at the center of the adjacent distances of the through holes 5 provided in the outer wall 2 and the inner wall 3 and formed as the elongated holes because the impression material loaded in the same position within the tray simultaneously enters into the through holes 5 and the circular through holes 6 and is pushed out of the tray at a time of loading the silicone impression material or the alginate impression material in the tray and pressing to the lower jaw within the oral cavity of the patient so as to take the impression, whereby a space is generated in the set impression material, and a phenomenon that the impression material is not closely attached to the lower jaw of the patient is created, so that there is a possibility that a good impression taking cannot be carried out. If the diameter of the circular through hole 6 is less than 3 mm, there is not created the effect that the impression material sufficiently enters into the circular through holes 6 so as to be retained at a time of loading the silicone impression material or the alginate impression material in the tray and pressing to the lower jaw within the oral cavity of the patient so as to take the impression. Accordingly, this diameter is not preferable. If the diameter goes beyond 6 mm, the impression material enters into the circular through holes 6 too much, and the phenomenon that the impression material is not closely attached to the lower jaw of the patient is created, so that there is a possibility that the good impression taking cannot be carried out.

Reference numeral 7 denotes a bottom portion through hole which is provided on a line connecting end portions in the bottom portion side of the elongated through holes 5 positioned at the closest sides to the end portions of the U-shaped portion in the outer wall 2 and the inner wall 3 in the end portions of the U-shaped portion of the bottom portion 1 or a side closer to the end portion than the line, has a width from 1.0 to 3.0 mm and a length from 5 to 15 mm, and is formed as an elongated hole. Since the bottom portion through holes 7 are provided, the impression material loaded in the closest side to the back tooth within the tray enters into each of the elongated through holes 5 which are provided in the outer wall 2 and the inner wall 3 in the end portion of the U-shaped portion and the elongated bottom portion through holes 7 which are provided in the bottom portion so as to be firmly retained, even if the height of the end portion side of the U-shaped in the outer wall 2 is reduced in conformity to the shape within the oral cavity. Accordingly, there is not generated the defect that the impression material in the end portion side (the back tooth side) of the U-shaped portion tends to be peeled off. In the bottom portion through hole 7 formed as the elongated hole and provided for achieving the effect mentioned above, in the case that the width thereof is less than 1.0 mm, there is not generated the effect that the impression material sufficiently enters into the bottom portion through holes 7 so as to be retained at a time of loading the silicone impression material or the alginate impression material in the tray and pressing to the lower jaw within the oral cavity of the patient so as to take the impression. Therefore, this width is not preferable. Further, if the width goes beyond 3.0 mm, the impression material enters into the bottom portion through holes 7 too much. Accordingly, there is generated the phenomenon that the impression material in the end portion of the U-shaped portion in the bottom portion 1 is not closely attached to the lower jaw of the patient, and there is a possibility that a good impression taking cannot be carried out.

Reference numeral 8 denotes a handle portion in the bottom portion 1 which is provided in the bottom surface of a center portion of the U-shaped portion. The handle portion may be fixed to the bottom portion 1 or may be structured such as to be detachably provided in the bottom surface of the center portion of the U-shaped portion in the bottom portion 1 as described in Japanese Patent Application No. 2011-217753 which was proposed by the applicant of the present patent application.

In the impression tray for a lower jaw according to the present invention mentioned above, in the case that the impression taking is carried out by loading the paste-like silicone impression material or alginate impression material on the bottom portion 1 of the U-shaped portion between the outer wall 2 and the inner wall 3 and pressing to the lower jaw within the oral cavity of the patient, the impression material is expanded to the outer wall 2 side and the inner wall 3 side and comes into contact with the undercut portion below the rim 4. Accordingly, the impression material can be prevented from floating upward and being peeled off from the tray after being set. Further, the impression material appropriately enters into the through holes 5 each of which reaches the bottom portion 1 from the portion just below the rim 4 vertically to the rims 4 of the outer wall 2 and the inner wall 3, has the width from 1.5 to 4.0 mm and is formed as the elongated hole, and into the circular through holes 6 each of which is formed in the bottom portion 1 positioned at the center of the adjacent distances of the through holes 5 which are provided in the outer wall 2 and the inner wall 3 and are formed as the elongated holes and has the diameter from 3 to 6 mm, and the set impression material is retained. The effect of retaining the set impression material mentioned above becomes higher in the case that the width of the elongated through hole is from 2.0 to 3.0 mm and the length is from 2 to 3 times the width, and the case that the distance between the elongated through holes is from 3 to 18 mm, and these cases are preferable.

Further, in the end portion of the U-shaped portion in the bottom portion 1, the impression material loaded in the closest side to the back tooth within the tray enters into the bottom portion through holes 7 each of which is provided on the line connecting the bottom portion side end portions of the through holes 5 which are positioned in the closest side to the end portion of the U-shaped portion in the outer wall 2 and the inner wall 3 and are formed as the elongated holes, or in the side closer to the end portion than the line, has the width from 1.0 to 3.0 mm and the length from 5 to 15 mm and is formed as the elongated hole, and into the through holes 5 which are positioned in the closest side to the end portion of the U-shaped portion of the outer wall 2 and the inner wall 3 in both sides thereof and are formed as the elongated holes, and the impression material is firmly retained. Therefore, there is not generated the defect that the impression material in the end portion side (the back tooth side) of the U-shaped portion tends to be peeled off.

As mentioned above, in the impression tray for a lower jaw according to the present invention, in addition to the effect of the undercut portion by the rim 4 which is provided in the bottom portion 1 side along each of the upper ends of the outer wall 2 and the inner wall 3, the impression material loaded on the tray enters into the through holes 5 each of which reaches the bottom portion 1 from the portion just below the rim 4 vertically to the rims 4 of the outer wall 2 and the inner wall 3, is provided at the particular width and distance and is formed as the elongated hole, into the circular through holes 6 each of which is formed in the bottom portion 1 positioned at the center of the adjacent distances of the elongated through holes 5 provided in the outer wall 2 and the inner wall 3 and has the particular diameter, into the bottom portion through holes 7 each of which is provided on the line connecting the bottom portion side end portions of the through holes 5 which are positioned at the closest side to the end portions of the U-shaped portion in the outer wall 2 and the inner wall 3 or in the closer side to the end portion than the lines, has the particular width and is formed as the elongated hole, and into the through holes 5 each of which is positioned in the closest side to the end portion to the end portion of the U-shaped portions of the outer wall 2 and the inner wall 3 in both sides thereof and is formed as the elongated hole, and the impression material is firmly retained. Therefore, since it is possible to prevent the set impression material from floating upward and being peeled off from the tray, it is possible to take the impression with high accuracy.

What is claimed is:

1. An impression tray for a lower jaw, comprising:
    a bottom portion which forms a U-shaped flat surface with an approximately uniform width;
    an outer wall which is inclined to an outer side of the impression tray via a circular arc shaped portion from an outer side of the bottom portion and is reduced its height in an end portion side of the U-shaped portion;
    an inner wall which is inclined to an inner side of the impression tray via a circular arc shaped portion from an inner side of said bottom portion;
    a rim having a height from 0.01 to 1 mm provided in said bottom portion along an upper end of said outer wall and an upper end of said inner wall;
    elongated through holes, each of which reaches said bottom portion from a portion just below said rim vertically and is formed as an elongated hole having a width from 1.5 to 4.0 mm, formed in such a manner that a distance between an adjacent pair of the elongated through holes is from 2 to 5 times the width of the elongated through hole;
    circular through holes provided in said bottom portion, each having a diameter from 3 to 6 mm and being positioned at the center of a distance between an adjacent pair of the elongated through holes which are provided in said outer wall and at the center of a distance between an adjacent pair of the elongated through holes which are provided in the inner wall; and
    bottom portion through holes, each of which has a width from 1.0 to 3.0 mm and a length from 5 to 15 mm and is formed as an elongated hole, formed on a line which connects the bottom portion side end portions of the respective elongated through holes positioned closest to the end portions of the U-shaped portion in said outer wall and the inner wall, or sides which are closer to the end portions than said line,
    wherein the impression tray is made of a plastic.

2. The impression tray for a lower jaw according to claim 1, wherein the width of the elongated through holes which are provided in the outer wall and the inner wall is from 2.0 to 3.0 mm, and the length is from 2 to 3 times the width.

3. The impression tray for a lower jaw according to claim 1, wherein the distance between an adjacent pair of the elongated through holes which are provided in the outer wall and the inner wall is from 3 to 18 mm.

4. The impression tray for a lower jaw according to any one of claim 1 or 2, wherein the height of the rim is from 0.1 to 0.3 mm.

5. The impression tray for a lower jaw according to any one of claim 1 or 2, wherein a rim having a height from 0.01 to 1 mm is provided in an opposite side to the bottom portion along each of the upper ends of the outer wall and the inner wall.

6. The impression tray for a lower jaw according to any one of claim 1 or 2, wherein only a single one of the circular through holes is positioned at the center of each adjacent pair of the elongated through holes provided in said outer wall and at the center of each adjacent pair of the elongated through holes provided in the inner wall.

7. The impression tray for a lower jaw according to any one of claim 1 or 2, wherein the bottom portion through holes are positioned closer to the end portions of the U-shaped portion than any of the circular through holes.

8. The impression tray for a lower jaw according to any one of claim 1 or 2, wherein the circular through holes are not positioned on a line connecting one of the elongated through holes provided in said outer wall with an adjacent one of the through holes provided in the inner wall.

* * * * *